(12) United States Patent
Blagg et al.

(10) Patent No.: US 9,447,092 B2
(45) Date of Patent: Sep. 20, 2016

(54) PHARMACEUTICALLY ACTIVE COMPOUNDS

(71) Applicant: CANCER RESEARCH TECHNOLOGY LIMITED, London (GB)

(72) Inventors: Julian Blagg, Sutton (GB); Vassilios Bavetsias, Sutton (GB); Andrew S. Moore, Herston (AU); Spyridon Linardopoulos, Sutton (GB)

(73) Assignee: CANCER RESEARCH TECHNOLOGY LIMITED, London (GB)

( * ) Notice: Subject to any disclaimer, the term of this patent is extended or adjusted under 35 U.S.C. 154(b) by 0 days.

(21) Appl. No.: 14/409,042

(22) PCT Filed: Jun. 21, 2013

(86) PCT No.: PCT/GB2013/051633
§ 371 (c)(1),
(2) Date: Dec. 18, 2014

(87) PCT Pub. No.: WO2013/190319
PCT Pub. Date: Dec. 27, 2013

(65) Prior Publication Data
US 2015/0266868 A1 Sep. 24, 2015

(30) Foreign Application Priority Data
Jun. 21, 2012 (GB) .................. 1211021.9

(51) Int. Cl.
*C07D 471/04* (2006.01)
*A61K 31/496* (2006.01)
*C07D 471/06* (2006.01)

(52) U.S. Cl.
CPC ........... *C07D 471/04* (2013.01); *C07D 471/06* (2013.01)

(58) Field of Classification Search
None
See application file for complete search history.

(56) References Cited

FOREIGN PATENT DOCUMENTS

| WO | WO 97/22596 | 6/1997 |
|---|---|---|
| WO | WO 97/30035 | 8/1997 |
| WO | WO 97/32856 | 9/1997 |
| WO | WO 98/13354 | 4/1998 |
| WO | WO 99/02166 | 1/1999 |
| WO | WO 00/40529 | 7/2000 |
| WO | WO 00/41669 | 7/2000 |
| WO | WO 01/92224 | 12/2001 |
| WO | WO 01/94341 | 12/2001 |
| WO | WO 02/04434 | 1/2002 |
| WO | WO 02/08213 | 1/2002 |
| WO | WO 2007/072017 | 6/2007 |
| WO | WO 2009/001021 | 12/2008 |

OTHER PUBLICATIONS

Fathi et al. Curr Opin Hematol. Mar. 2011 ; 18(2): 71-76.*
Boss et al. The Oncologist 2009;14:780-793.*
Bavetsias, V. et al., "Optimization of Imidazo[4,5-b]pyridine-Based Kinase Inhibitors: Identification of a Dual FLT3/Aurora Kinase Inhibitor as an Orally Bioavailable Preclinical Development Candidate for the Treatment of Acute Myeloid Leukemia", *J. Med. Chem.*, 2012, 55, 8721-8734.
Lan, P. et al., "Molecular modeling studies on imdazo[4,5-b]pyridine derivatives as Aurora A kinase inhibitors using 3D-QSAR and docking approaches", *European Journal of Medicinal Chemistry*, 2011, 46, 77-94.
Faisal, A. et al., "The Aurora Kinase Inhibitor CCT137690 Downregulates MYCN and Sensitizes *MYCN*-Amplified Neuroblastoma In Vivo", *Mol. Cancer. Ther.*, 2011, 10, 2115-2123.
PCT International Search Report/Written Opinion prepared for PCT/GB2013/051633, mailed Sep. 8, 2013.
UK Search Report/Written Opinion prepared for GB1211021.9, mailed Oct. 16, 2012.

* cited by examiner

*Primary Examiner* — Emily Bernhardt
(74) *Attorney, Agent, or Firm* — Barnes & Thornburg LLP (57) ABSTRACT

The present invention relates to compounds of formula I: wherein $R_1$ and $R_2$ are as defined herein, or a pharmaceutically acceptable salt or solvate thereof. The compounds of formula I are inhibitors of aurora kinase and/or FLT3. The present invention also relates to processes for the preparation of these compounds, to pharmaceutical compositions comprising them, and to their use in the treatment of proliferative disorders, such as cancer, as well as other diseases or conditions in which aurora kinase and/or FLT3 activity is implicated.

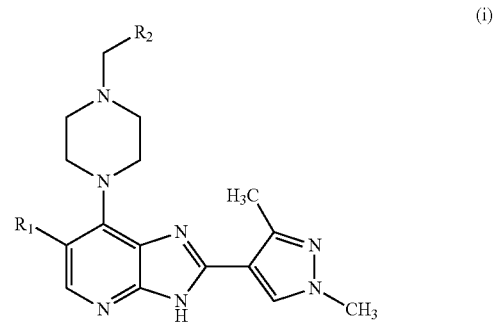

9 Claims, 2 Drawing Sheets

PHARMACEUTICALLY ACTIVE COMPOUNDS

CROSS-REFERENCE TO RELATED APPLICATIONS

This application is a national stage entry under 35 USC §371(b) of PCT International Application No. PCT/GB2013/051633, filed Jun. 21, 2013, and claims the benefit of United Kingdom Patent Application No. 1211021.9, filed on Jun. 21, 2012, both of which are expressly incorporated by reference herein.

INTRODUCTION

The present invention relates to pharmaceutically active compounds. More specifically, the present invention relates to compounds that are inhibitors of Aurora kinase enzyme activity. The compounds of the invention are also inhibitors of FMS-like tyrosine kinase 3 (FLT3) activity. The present invention also relates to processes for the preparation of these compounds, to pharmaceutical compositions comprising them, and to their use in the treatment of proliferative disorders, such as cancer, as well as other diseases or conditions in which Aurora kinase and/or FLT3 activity is implicated.

BACKGROUND OF THE INVENTION

Proliferative diseases, such as cancer, are characterised by uncontrolled and unregulated cellular proliferation. Precisely what causes a cell to proliferate in an uncontrolled and unregulated manner has been the focus of intense research over recent decades.

Aurora kinases, a family of three serine-threonine kinases designated as A, B, and C, play key and distinct roles in different stages of mitosis.[1-3] At the early stages of mitosis, Aurora-A forms a complex with the targeting protein for Xklp2 (TPX2) that regulates centrosome maturation and mitotic spindle assembly.[4,5] Aurora-B forms complexes with the inner centromere protein (INCENP), survivin and borealin thereby regulating chromosome condensation, chromosome alignment, mitotic checkpoint and cytokinesis.[6-9] Over expression of Aurora-A and Aurora-B has been reported in a wide range of human malignancies including breast, colorectal, ovarian, glioma, thyroid carcinoma, and seminoma.[10-16] The function of Aurora-C during mitosis is less well understood. However, high expression of Aurora-C has been reported in the testis.[17,18]

In recent years, small-molecule targeting of Aurora kinases has been become a common strategy for the discovery of new cancer chemotherapeutics, and a number of structurally diverse inhibitors of Aurora activity have been reported,[18-20] including 1 (VX-680 (MK-0457)),[21] 2 (AZD1152)[22], 3 (PHA-739358),[23,24] and 4 (AMG 900)[25] (see below).

1. VX-680 (MK-0457)
2. AZD1152
3. PHA-739358
4. AMG 900

However, there remains a need to identify further therapeutic agents capable of inhibiting Aurora kinase activity.

International Patent Publication Nos. WO2007/072017 and WO2009/001021 both disclose a series of imidazo[4,5-b]pyridine derivatives that function as inhibitors of Aurora kinase activity, and which are therefore potentially useful therapeutic agents for the treatment of cancer. One particular compound disclosed in WO2009/001021 is shown below.

This particular compound (known as CCT137690) is a potent and orally bioavailable inhibitor of Aurora kinases that inhibits the growth of a SW620 human colon carcinoma xenograft in vivo with concomitant biomarker modulation consistent with target engagement.[26] However, the preclinical development of this compound was limited because of its narrow safety margin against hERG[43] ($IC_{50}$=3.0 μM)[26] and its low human liver microsomal stability (86% metabolised after a 30 min incubation, unpublished data).

It is therefore an object of the present invention to provide orally bioavailable inhibitors of Aurora kinase enzyme activity are suitable for preclinical and clinical evaluation.

It is therefore an object of the present invention to provide orally bioavailable inhibitors of Aurora kinase enzyme activity that possess acceptable human microsomal stability, reduced inhibition of cytochrome $P_{450}$ activity and, in the case of certain compounds, a wider therapeutic index against hERG.

FLT3 is a trans-membrane kinase that belongs to the class III receptor tyrosine kinase (RTK) family. Binding of FLT3-ligand (FL) to its receptor leads to dimerisation, autophosphorylation and subsequent activation of downstream signalling pathways[37]. High levels of FLT3 expression have been found in acute myeloid leukaemia (AML) blasts, and two major classes of mutations, i.e. internal-tandem duplications (ITDs) and tyrosine kinase domain (TKD) point mutations, have been identified in AML patients[37,38]. Internal-tandem duplications are detected in 20-25% of AML patients, and tyrosine kinase domain point mutations in 5-10% of AML patients[37,38]. A number of small-molecule inhibitors of FLT3 have been evaluated in clinical trials[38,39].

There is, therefore, a further need for compounds that have a dual function of inhibiting both Aurora kinases and FLT3. Such compounds would be useful for the treatment of diseases and/or conditions in which Aurora and/or FLT3 are implicated, such as, for example, AML.

It is therefore a further object of the present invention to provide compounds possessing this dual activity.

SUMMARY OF THE INVENTION

In one aspect, the present invention provides a compound, or a pharmaceutically acceptable salt or solvate thereof as defined herein.

In another aspect, the present invention provides a pharmaceutical composition comprising a compound of the invention as defined herein, or a pharmaceutically acceptable salt or solvate thereof, and one or more pharmaceutically acceptable excipients.

In another aspect, the present invention relates to a compound of the invention as defined herein, or a pharmaceutically acceptable salt or solvate thereof, or a pharmaceutical composition as defined herein, for use in therapy.

In another aspect, the present invention relates to a compound of the invention as defined herein, or a pharmaceutically acceptable salt or solvate thereof, or a pharmaceutical composition as defined herein, for use in the treatment of diseases or conditions in which Aurora kinase and/or FLT3 activity is implicated.

In another aspect, the present invention relates to the use of a compound of the invention as defined herein, or a pharmaceutically acceptable salt or solvate thereof, in the manufacture of a medicament for use in the treatment of diseases or conditions in which Aurora kinase and/or FLT3 activity is implicated.

In another aspect, the present invention relates to a method of treating a disease or condition in which Aurora kinase and/or FLT3 activity is implicated, said method comprising administering to a subject in need of such treatment a therapeutically effective amount of a compound of the invention as defined herein, or a pharmaceutically acceptable salt or solvate thereof, or a pharmaceutical composition as defined herein.

In another aspect, the present invention provides a compound, or a pharmaceutically acceptable salt or solvate thereof, or a pharmaceutical composition as defined herein, for use in the treatment of a proliferative disorder, such as cancer. In a particular embodiment, the cancer is a human cancer.

In another aspect, the present invention provides the use of a compound, or a pharmaceutically acceptable salt or solvate thereof, in the manufacture of a medicament for use in the treatment of a proliferative disorder, such as cancer. In a particular embodiment, the cancer is a human cancer.

In another aspect, the present invention provides a method of treating a proliferative disorder, such as cancer, said method comprising administering to a subject in need of such treatment a therapeutically effective amount of a compound, or a pharmaceutically acceptable salt or solvate thereof, or a pharmaceutical composition as defined herein. In a particular embodiment, the cancer is a human cancer.

In another aspect, the present invention provides a compound, or a pharmaceutically acceptable salt or solvate thereof, or a pharmaceutical composition as defined herein, for use in the production of an Aurora kinase and/or FLT3 inhibitory effect.

In another aspect, the present invention provides the use of a compound, or a pharmaceutically acceptable salt or solvate thereof, in the manufacture of a medicament for use in the production of an Aurora kinase and/or FLT3 inhibitory effect.

In another aspect, the present invention provides a method of producing an Aurora kinase and/or FLT3 inhibitory effect in vitro, said method comprising administering an effective amount of a compound, or a pharmaceutically acceptable salt or solvate thereof.

In another aspect, the present invention provides a method of producing an Aurora kinase and/or FLT3 inhibitory effect in vivo, said method comprising administering an effective amount of a compound, or a pharmaceutically acceptable salt or solvate thereof.

In another aspect, the present invention provides a method of inhibiting cell proliferation in vitro or in vivo, said method comprising contacting a cell with an effective amount of a compound as defined herein, or a pharmaceutically acceptable salt or solvate thereof.

The present invention further provides a method of synthesising a compound, or a pharmaceutically acceptable salt or solvate thereof, as defined herein.

In another aspect, the present invention provides a compound, or a pharmaceutically acceptable salt or solvate thereof, obtainable by, or obtained by, or directly obtained by a method of synthesis as defined herein.

In another aspect, the present invention provides novel intermediates as defined herein which are suitable for use in any one of the synthetic methods set out herein.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The phrase "compound of the invention" means those compounds which are disclosed herein, both generically and specifically.

Compounds of the Invention

As previously stated, International Patent Publication No. WO2007/072017 discloses a series of imidazo[4,5-b]pyridine derivatives that function as inhibitors of Aurora kinase activity. Two particular compounds disclosed in WO2007/072017 are 6-bromo-2-(1-methyl-1H-pyrazol-4-yl)-7-(4-(pyridine-3-ylmethyl)piperazin-1-yl)-3H-imidazo[4,5-b]pyridine (Example 56) and 6-bromo-7-(4-(pyridine-3-ylmethyl)piperazin-1-yl)-2-(1,3,5-trimethyl-1H-pyrazol-4-yl)-3H-imidazo[4,5-b]pyridine (Example 57). The structures of these compounds are shown below.

Example 56, WO2007/072017

Example 57, WO2007/072017

In a first aspect, the present invention provides a compound of formula I shown below:

wherein:

R$_1$ is Br or Cl;

R$_2$ is selected from formula II or formula III shown below:

II wherein $R_a$ is hydrogen or methyl;
or a pharmaceutically acceptable salt or solvate thereof.

In the definition of the $R_2$ group above, the symbol ⌇ denotes the point attachment of the $R_2$ group to the —$CH_2$— moiety present in the compounds of formula I.

The compounds of the present invention demonstrate reduced inhibition of cytochrome $P_{450}$ activity relative to the compounds of Examples 56 and 57 in WO2007/072017. Certain compounds of the present invention also possess a wider therapeutic index against hERG relative to the compounds of Examples 56 and 57 in WO2007/072017.

Particular compounds of the invention include, for example, compounds of the formula I, or pharmaceutically acceptable salts thereof, wherein, unless otherwise stated, each of $R_1$ and $R_2$ has any of the meanings defined hereinbefore or in any of paragraphs (1) to (5) hereinafter:

(1) $R_1$ is Br;
(2) $R_1$ is Cl;
(3) $R_2$ is of formula II;
(4) $R_2$ is of formula III as defined herein;
(5) $R_2$ is of formula III as defined herein and $R_a$ is hydrogen;
(6) $R_2$ is of formula III as defined herein and $R_a$ is methyl;

Suitably, $R_1$ is chloro.

Suitably, $R_2$ is of formula II (i.e. para-chlorophenyl). In a particular group of compounds of the invention, therefore, the compounds have the structural formula Ia shown below:

wherein $R_1$ is as defined hereinbefore, or a pharmaceutically acceptable salt or solvate thereof.

In a further group of compounds of the invention, $R_2$ is of formula III, i.e. the compounds have the structural formula Ib shown below:

wherein $R_1$ and $R_a$ are both as defined hereinbefore, or a pharmaceutically acceptable salt or solvate thereof.

Particular compounds of the present invention include any one of the following:

6-Chloro-7-(4-(4-chlorobenzyl)piperazin-1-yl)-2-(1,3-dimethyl-1H-pyrazol-4-yl)-3H-imidazo[4,5-b]pyridine;

3-((4-(6-Chloro-2-(1,3-dimethyl-1H-pyrazol-4-yl)-3H-imidazo[4,5-b]pyridin-7-yl)piperazin-1-yl)methyl)-1,2,4-oxadiazole;

3-((4-(6-Chloro-2-(1,3-dimethyl-1H-pyrazol-4-yl)-3H-imidazo[4,5-b]pyridin-7-yl)piperazin-1-yl)methyl)-5-methyl-1,2,4-oxadiazole;

or a pharmaceutically acceptable salt or solvate thereof.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid.

The present invention also encompasses compounds of the invention as defined herein which comprise one or more isotopic substitutions. For example, H may be in any isotopic form, including $^1H$, $^2H(D)$, and $^3H$ (T); C may be in any isotopic form, including $^{12}C$, $^{13}C$, and $^{14}C$; and the like.

It is also to be understood that certain compounds of the invention may exist in solvated as well as unsolvated forms such as, for example, hydrated forms. It is to be understood that the invention encompasses all such solvated forms that possess Aurora kinase and/or FLT3 inhibitory activity.

It is also to be understood that certain compounds of the invention may exhibit polymorphism, and that the invention encompasses all such forms that possess Aurora kinase and/or FLT3 inhibitory activity.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms of the compounds of the present invention include the compounds in the form shown in formula I above as well as tautomers of the formula (IV) and (V) shown below.

wherein $R_1$ and $R_2$ are as defined hereinbefore.

Compounds of the invention containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The compounds of the invention may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable amide derivatives that may be formed at an amino group in a compound of the invention.

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically acceptable pro-drug of a compound of the formula I is one that is based on reasonable medical judgement as being suitable for administration to the human or animal body without undesirable pharmacological activities and without undue toxicity.

Various forms of pro-drug have been described, for example in the following documents:
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

It shall also be appreciated that compounds of formula I may also be covalently linked (at any suitable position) to other groups such as, for example, solubilising moieties (for example, PEG polymers), moieties that enable them to be bound to a solid support (such as, for example, biotin-containing moieties), and targeting ligands (such as antibodies or antibody fragments).

Synthesis

In the description of the synthetic methods described below and in the referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3.OEt_2$. A suitable alternative protecting group for a primary amino group is, for example, a phthaloyl group which may be removed by treatment with an alkylamine, for example dimethylaminopropylamine, or with hydrazine.

The compounds of the present invention may be prepared by using the general synthetic techniques described in WO2007/072017 and WO2009/001021, the entire contents of which are incorporated herein by reference.

In a particular aspect, the present invention provides a method of synthesising a compound of the formula I, or a pharmaceutically acceptable salt or solvate thereof, the method comprising:

a) reacting a compound of formula A:

A wherein $R_1$ and $R_2$ each have any one of the meanings set out hereinbefore;
with 1,3-dimethyl-1H-pyrazole-4-carbaldehyde in the presence of a suitable reducing agent; and b) optionally thereafter, and if necessary:
i) removing any protecting groups present;
ii) converting the compound formula I into another compound of formula I; and/or
iii) forming a pharmaceutically acceptable salt or solvate thereof.

Suitably the reaction between the compound of formula A and 1,3-dimethyl-1H-pyrazole-4-carbaldehyde takes place in the presence of a suitable solvent. Any suitable solvent or solvent mixture may be used for this reaction. Examples of suitable solvents include DMSO, water, DMF, and alcohols e.g. EtOH.

Suitably, the reaction the proceeds in the presence of a suitable reducing agent, such as aqueous $Na_2S_2O_4$.[26]

A person skilled in the art will also be able to select appropriate reaction conditions to use in order to facilitate this reaction.

The reaction may also be carried out an elevated temperature, for example a temperature within the range of 50 to 190° C. may be used (depending on the nature of the solvent).

The resultant compound of formula I can be isolated and purified using techniques well known in the art.

The process defined herein may further comprise the step of subjecting the compound of formula I to a salt exchange, particularly in situations where the compound of formula I is formed as a mixture of different salt forms. The salt exchange suitably comprises immobilising the compound of formula I on a suitable solid support or resin, and eluting the compounds with an appropriate acid to yield a single salt of the compound of formula I.

The compounds of formula A can be prepared by processes known in the art.

An example of a suitable procedure for the preparation of the compound of Formula I via an intermediate of formula A is shown in Scheme 1 below.

Scheme 1

Reagents and conditions: steps (a) and (b) above relate only to the 1,2,4-oxadiazole derivative because 1-(4-chlorobenzyl)piperazine and 1-((5-methyl-1,2,4-oxadiazol-3-yl)methyl)piperazine are commercially available:
a for 1,2,4-oxadiazole derivative: $CH_2Cl_2$, 3-(chloromethyl)-1,2,4-oxadiazole, $Et_3N$, 50° C.;
b for 1,2,4-oxadiazole derivative: TFA, $CH_2Cl_2$, room temp.;
c for 4-chlorobenzyl and 1,2,4-oxadiazole derivatives: 2-amino-4,5-dichloro-3-nitropyridine, $^iPr_2NEt$, $^iPrOH$, heating;
d for 4-chlorobenzyl and 1,2,4-oxadiazole derivatives: 1,3-dimethyl-1H-pyrazole-4-carbaldehyde, EtOH, 1M aq. $Na_2S_2O_4$, 80° C.

2-Amino-4,5-dichloro-3-nitropyridine (4,5-dichloro-3-nitropyridin-2-amine) and 2-amino-5-bromo-4-chloro-3-nitropyridine (5-bromo-4-chloro-3-nitropyridin-2-amine), precursors for the synthesis of 2-amino-3-nitropyridine derivatives A, were prepared as previously described [26] or by halogenation of 2-amino-4-chloro-3-nitropyridine (4-chloro-3-nitropyridin-2-amine)[40].

Pharmaceutical Compositions

According to a further aspect of the invention there is provided a pharmaceutical composition which comprises a compound of the invention as defined hereinbefore, or a pharmaceutically acceptable salt or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of proliferative disease is an amount sufficient to symptomatically relieve in a warm-blooded animal, particularly a human the symptoms of infection, to slow the progression of infection, or to reduce in patients with symptoms of infection the risk of getting worse.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, 0.1 mg/kg to 30 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The compounds of the invention are inhibitors of Aurora kinase and FLT3 activity.

Thus, in another aspect, the present invention provides a method of inhibiting Aurora kinase activity and/or FLT3 in a cell, the method comprising administering to said cell compound of formula I as defined herein, or a pharmaceutically acceptable salt or solvate thereof.

In a further aspect, the present invention provides a method of inhibiting Aurora kinase activity and/or FLT3 in vitro or in vivo, said method comprising contacting a cell with an effective amount of a compound, or a pharmaceutically acceptable salt or solvate thereof, as defined herein.

In another aspect, the present invention provides a method of inhibiting Aurora kinase activity and/or FLT3 in a human or animal subject in need of such inhibition, the method comprising administering to said subject an effective amount of a compound of formula I as defined herein, or a pharmaceutically acceptable salt or solvate thereof.

The Aurora kinase may be Aurora kinase A, B or C.

In one aspect, the present invention provides a compound of Formula I, or a pharmaceutically acceptable salt or solvate thereof, or a pharmaceutical composition as defined herein for use in therapy.

In another aspect, the present invention provides a compound of formula I as defined herein, or a pharmaceutically acceptable salt or solvate thereof for use in the treatment of disease or condition associated with Aurora kinase activity (and/or FLT3 activity).

In another aspect, the present invention provides the use of a compound of formula I as defined herein, or a pharmaceutically acceptable salt or solvate thereof, in the manufacture of a medicament for use in the treatment of disease or condition associated with Aurora kinase activity (and/or FLT3 activity).

In yet another aspect, the present invention provides a method of treating a proliferative disorder in a human or animal subject, the method comprising administering to said subject a therapeutically acceptable amount of a compound of formula I as defined herein, or a pharmaceutically acceptable salt or solvate thereof.

In yet another aspect, the present invention provides a compound of formula I as defined herein, or a pharmaceutically acceptable salt or solvate thereof, for use in the treatment of a proliferative disorder.

In yet another aspect, the present invention provides the use of a compound of formula I as defined herein, or a pharmaceutically acceptable salt or solvate thereof, in the manufacture of a medicament for use in the treatment of a proliferative disorder.

In another aspect, the present invention provides a compound, or a pharmaceutically acceptable salt or solvate thereof, or a pharmaceutical composition as defined herein for use in the treatment of cancer.

In yet another aspect, the present invention provides the use of a compound, or a pharmaceutically acceptable salt or solvate thereof, as defined herein in the manufacture of a medicament for use in the treatment of cancer.

In yet another aspect, the present invention provides a method of treating cancer in a patient in need of such treatment, said method comprising administering to said patient a therapeutically effective amount of a compound, or a pharmaceutically acceptable salt or solvate thereof, or a pharmaceutical composition as defined herein.

The compounds of the invention may be useful, for example, for the treatment of colorectal, breast, lung, prostate, pancreatic or bladder and renal cancer or leukaemias or lymphomas.

In particular, the compounds of the present invention are useful for the treatment of leukaemias. High expression of Aurora kinases has been demonstrated in leukaemia (cell lines and patient cohorts).[30-33] In addition, internal tandem duplication of the FLT3 gene (FLT3-ITD) results in constitutive FLT3 kinase activation.[34] Significantly, FLT3-ITD occurs in 20-35% of adults and 15% of children with AML conferring a poor prognosis in both age groups.[35]

Thus, in a particular embodiment, the compounds are useful for treating leukaemias such as acute myeloid leukaemia (AML), myelodysplastic syndrome (MDS), chronic lymphocytic leukaemia (CLL) and multiple myeloma. The compounds of the present invention are also envisaged to be useful for the treatment of neuroblastoma, The compounds of the present invention are expected to be of particular benefit in patients that have failed treatment with standard therapies. It predicted that the compounds of the present invention will also be of value for the treatment of older patients (e.g. over 60 years old) with leukaemia, (e.g. AML) because such patients are expected to benefit for aurora kinase inhibition.

The compounds of the present invention are also expected to be of value in the treatment of children with leukaemia (e.g. newly diagnosed FLT3-mutated AML and infant AML), as well as neuroblastomas.

Routes of Administration

The compounds of the invention or pharmaceutical composition comprising the active compound may be administered to a subject by any convenient route of administration, whether systemically/peripherally or topically (i.e. at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The compounds of the invention may be administered alone as a monotherapy or may administered in combination with one or more additional therapeutic agents. The selection of the one or more additional therapeutic agents will of course vary depending on the disease or condition to be treated and its severity.

It is commonplace to use combination therapies to treat proliferative disorders, such as cancer. Therefore, the antiproliferative treatment defined hereinbefore may be applied as a sole therapy or may involve, in addition to the compound of the invention, conventional surgery or radiotherapy or chemotherapy. Such chemotherapy may include one or more of the following categories of anti-tumour agents:

(i) other antiproliferative/antineoplastic drugs and combinations thereof, as used in medical oncology, such as alkylating agents (for example cisplatin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab [Vectibix®], the anti-erbB1 antibody cetuximab [Erbitux®, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, PIt3 kinase inhibitors, CSF-1R kinase inhibitors, IGF receptor (insulin-like growth factor) kinase inhibitors; Aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including, for example, using the compounds of the invention in combination with oncolytic adenoviruses approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint/combination treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to a particular aspect of the invention there is provided a combination suitable for use in the treatment of a disease or condition in which protein kinase activity is implicated as defined herein (e.g. cancer), comprising a compound of the invention as defined hereinbefore, or a pharmaceutically acceptable salt or solvate thereof, and another therapeutic agent (e.g. an anti-tumour agent).

According to this aspect of the invention there is provided a combination suitable for use in the treatment of a cancer (for example a cancer involving a solid tumour) comprising a compound of the invention as defined hereinbefore, or a pharmaceutically acceptable salt or solvate thereof, and any one of the anti-tumour agents listed under (i)-(ix) above.

In a further aspect of the invention there is provided a compound of the invention or a pharmaceutically acceptable salt or solvate thereof, in combination with an anti-tumour agent selected from one listed under (i)-(ix) herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt or solvate thereof in combination with one or more additional therapeutic agents (for example, an anti-tumour agent selected from one listed under (i)-(ix) herein above), in association with a pharmaceutically acceptable diluent or carrier.

The compounds of the present invention are expected to be particularly useful as part of a combination therapy with the existing standard of care for the treatment of older patients (i.e. patients over 60 years old), as such patients may well benefit for Aurora kinase inhibition (regardless of their FLT3 status).

The compounds of the present invention are also expected to be particularly useful as part of combination therapy with the existing standard of care for the treatment of children suffering from with leukaemia (e.g. AML) or neuroblastoma.

BRIEF DESCRIPTION OF THE FIGURES

Tumour samples were obtained 2 h after the final dose. Total histone H3, total Stat5 and GAPDH were used as loading controls.

EXAMPLES

Synthesis of Compounds

Examples 1 to 3

General Materials and Methods

Commercially available starting materials, reagents and dry solvents were used as supplied. Flash column chromatography was performed using Merck silica gel 60 (0.025-0.04 mm). Column chromatography was also performed on a FlashMaster personal unit using isolute Flash silica columns or a Biotage SP1 purification system using Biotage Flash silica cartridges. Preparative TLC was performed on Analtech or Merck plates. Ion exchange chromatography was performed using acidic Isolute Flash SCX-II cartridges. $^1$H NMR spectra were recorded on a Bruker Avance-500. Samples were prepared as solutions in a deuterated solvent and referenced to the appropriate internal non-deuterated solvent peak or tetramethylsilane. Chemical shifts were recorded in ppm (δ) downfield of tetramethylsilane. LC-MS analysis was performed on a Waters LCT with a Waters Alliance 2795 separations module and Waters 2487 dual wavelength absorbance detector coupled to a Waters/Micromass LCT time of flight mass spectrometer with ESI source. Analytical separation was carried out at 30° C. either on a Merck Chromolith SpeedROD column (RP-18e, 50×4.6 mm) using a flow rate of 2 mL/min in a 3.5 minute gradient elution with detection at 254 nm or on a Merck Purospher STAR column (RP-18e, 30×4 mm) using a flow rate of 1.5 mL/min in a 3.5 minute gradient elution with detection at 254 nm. The mobile phase was a mixture of methanol (solvent A) and water (solvent B) both containing formic acid at 0.1%. Gradient elution was as follows: 1:9 (A/B) to 9:1 (A/B) over 2.25 min, 9:1 (A/B) for 0.75 min, and then reversion back to 1:9 (A/B) over 0.3 min, finally 1:9 (A/B) for 0.2 min).

LC-HRMS analysis was performed on an Agilent 1200 series HPLC and diode array detector coupled to a 6520 Quadrupole-Time of flight mass spectrometer with dual multimode APCI/ESI source. Analytical separation was carried out at 30° C. on a Merck Purospher STAR column (RP-18e, 30×4 mm) using a flow rate of 1.5 mL/min in a 4 minute gradient elution with detection at 254 nm. The mobile phase was a mixture of methanol (solvent A) and water (solvent B) both containing formic acid at 0.1%. Gradient elution was as follows: 1:9 (A/B) to 9:1 (A/B) over 2.5 min, 9:1 (A/B) for 1 min, and then reversion back to 1:9 (A/B) over 0.3 min, finally 1:9 (A/B) for 0.2 min. The following references masses were used for HRMS analysis: caffeine [M+H]$^+$ 195.087652; (hexakis(1H,1H,3H-tetrafluoropentoxy)phosphazene [M+H]$^+$ 922.009798) and hexakis (2,2-difluoroethoxy)phosphazene [M+H]$^+$ 622.02896 or reserpine [M+H]$^+$ 609.280657.

Example 1

Preparation of 6-Chloro-7-(4-(4-chlorobenzyl)piperazin-1-yl)-2-(1,3-dimethyl-1H-pyrazol-4-yl)-3H-imidazo[4,5-b]pyridine 4-Chloro-3-nitropyridin-2-amine[40]

To a 100 mL round-bottomed flask containing 2-amino-4-chloropyridine (0.480 g, 3.75 mmol) cooled in an ice bath was added concentrated sulphuric acid (5.4 g). The reaction mixture was stirred for 5 min and then nitric acid (70%; 0.36 g) was added dropwise. The reaction mixture was stirred at 0° C. for 10 min, then heated to 55° C. and stirred at this temperature for 1 h. It was cooled to room temperature and diluted with ice-water. The pH was carefully adjusted to ~7.5 with 10% aqueous NaOH whereupon a yellow precipitate formed. This was filtered off, washed with water and dried in vacuo over $P_2O_5$. The product was purified by silica column chromatography (elution with dichloromethane) to provide in order of elution: 4-Chloro-3-nitropyridin-2-amine as a yellow solid (0.210 g, 32%), $^1$H-NMR (500 MHz, DMSO-d$_6$) 6.87 (d, J=5.2 Hz, 1H, pyridine C—H), 7.21 (s, 2H, NH$_2$), 8.11 (d, J=5.2 Hz, 1H, pyridine C—H).

4-Chloro-5-nitropyridin-2-amine (0.080 g, 12%): $^1$H-NMR (500 MHz, DMSO-d$_6$) 6.58 (s, 1H, pyridine C—H) 7.58 (s, 2H, NH$_2$), 8.79 (s, 1H, pyridine C—H).

4,5-Dichloro-3-nitropyridin-2-amine

4-Chloro-3-nitropyridin-2-amine (0.10 g, 0.58 mmol) was dissolved in dry acetonitrile (20 mL). To the stirred solution was then added N-chlorosuccinimide (0.094 g, 0.70 mmol), and the reaction mixture was heated at 80° C. for 1 h. Volatiles were removed in vacuo and the residue purified by silica column chromatography (elution with dichloromethane) to provide the title compound as a pale brown powder (0.125 g, 85%). $^1$H-NMR (500 MHz, DMSO-d$_6$) 7.35 (s, 2H, NH$_2$), 8.36 (s, 1H, 6-H).

5-Chloro-4-(4-(4-chlorobenzyl)piperazin-1-yl)-3-nitropyridin-2-amine

To a mixture of 2-amino-4,5-dichloro-3-nitropyridine (0.152 g, 0.73 mmol) and isopropanol (22 mL) was added 1-(4-chlorobenzyl)piperazine (0.165 g, 0.78 mmol) followed by diisopropylethylamine (0.17 mL, 0.97 mmol). The reaction mixture was heated at 45° C. for 18 h, then allowed to cool to room temperature, and diluted with isopropanol (5 mL). The precipitate was collected by filtration, washed with isopropanol and diethyl ether. The title compound was thus obtained as a yellow solid (0.215 g, 77%); $^1$H-NMR (500 MHz, DMSO-$d_6$) 2.48 (br s, obscured by DMSO peak, 4H, piperazine C—H), 3.06 (br t, J=4.3 Hz, 4H, piperazine C—H), 3.52 (s, 2H, NCH$_2$C$_6$H$_4$Cl), 6.95 (s, 2H, NH$_2$), 7.35 (d, J=8.5 Hz, 2H) and 7.38 (d, J=8.5 Hz, 2H) (3,5-ArH and 2,6-ArH), 8.06 (s, 1H, 6-H); LC-MS (ESI, m/z): Rt=1.70 min-382, 384, 386 [(M+H)$^+$, Cl$_2$ isotopic pattern].

6-Chloro-7-(4-(4-chlorobenzyl)piperazin-1-yl)-2-(1,3-dimethyl-1H-pyrazol-4-yl)-3H-imidazo[4,5-b]pyridine To a mixture of 5-chloro-4-(4-(4-chlorobenzyl)piperazin-1-yl)-3-nitropyridin-2-amine (0.076 g, 0.20 mmol) and EtOH (4.0 mL) was added 1,3-dimethyl-1H-pyrazole-4-carbaldehyde (0.027 g, 0.22 mmol) followed by a freshly prepared aqueous solution of Na$_2$S$_2$O$_4$ (1M; 0.85 mL, 0.85 mmol). The reaction mixture was stirred at 80° C. for 24 h, it was then allowed to cool to room temperature, concentrated in vacuo, and the residue was absorbed on silica gel and placed on a 10 g isolute silica column. Elution with ethyl acetate/dichloromethane (v/v; 1:1), and then 4% methanol in ethyl acetate/dichloromethane (v/v; 1:1) afforded the title compound as a white solid after trituration with diethyl ether (0.023 g, 25%).

$^1$H-NMR (500 MHz, DMSO-$d_6$) 2.51 (s, obscured by solvent peak, pyrazole 3-CH$_3$), 2.57 (br s, 4H, piperazine C—H), 3.54 (s, 2H, N—CH$_2$C$_6$H$_4$Cl), 3.68 (br s, 4H, piperazine C—H), 3.84 (s, 3H, pyrazole N-Me), 7.37 (d, J=8.5 Hz, 2H) and 7.40 (d, J=8.5 Hz, 2H) (C$_6$H$_4$Cl), 8.02 (s, 1H), and 8.18 (s, 1H) (pyrazole 5-H, and imidazo[4,5-b]pyridine 5-H), 12.95 (br s, 1H, imidazo[4,5-b]pyridine N—H); LC-MS (ESI, m/z): Rt=1.97 min-456, 458, 460 [(M+H)$^+$, Cl$_2$ isotopic pattern].

HRMS: Found: 456.1457, calculated for C$_{22}$H$_{24}$Cl$_2$N$_7$ (M+H)$^+$: 456.1465.

This compound was also produced in bulk quantities ranging from 0.80 g to 1.80 g and in yields ranging from 54% to 70%. The same method was used as described above but during work-up, the reaction mixture was partitioned between water and chloroform. The aqueous layer was extracted with chloroform and ethyl acetate and the combined organics were dried and concentrated in vacuo. DMSO was also used as a solvent in place of EtOH, and in this occasion the reaction mixture was stirred at 120° C. for 3 h.

Example 2

Preparation of 3-((4-(6-Chloro-2-(1,3-dimethyl-1H-pyrazol-4-yl)-3H-imidazo[4,5-b]pyridin-7-yl)piperazin-1-yl)methyl)-1,2,4-oxadiazole tert-Butyl 4-((1,2,4-oxadiazol-3-yl)methyl)piperazine-1-carboxylate To a solution of Boc-piperazine (571 mg, 3.07 mmol) and 3-(chloromethyl)-1,2,4-oxadiazole (400 mg, 3.37 mmol) in CH$_2$Cl$_2$ (30 mL) was added triethylamine (1.70 mL, 12.3 mmol). The reaction was stirred for 22 h at 50° C. before concentrated in vacuo to give a crude oily white solid. Purification was accomplished by flash chromatography on silica gel (4×12) eluting with MeOH/CH$_2$Cl$_2$ (5%) to yield the title compound (555 mg, 67%) as a white solid. $^1$H-NMR (500 MHz, CDCl$_3$) 1.43 (s, 9H, C(CH$_3$)$_3$), 2.52 (app t, J=4.9 Hz, 4H, CH$_2$), 3.45 (app t, J=4.9 Hz, 4H, CH$_2$), 3.78 (s, 2H, CH$_2$C—), 8.71 (s, 1H, CH$_{ar}$); LC-MS (ESI, m/z): Rt=1.67 min-213 (M-$^t$Bu)$^+$, 169 (M-Boc)$^+$.

4-(4-((1,2,4-Oxadiazol-3-yl)methyl)piperazin-1-yl)-5-chloro-3-nitropyridin-2-amine To a solution of tert-butyl 4-((1,2,4-oxadiazol-3-yl)methyl)piperazine-1-carboxylate (213 mg, 0.790 mmol) in CH$_2$Cl$_2$ (18 mL) was added TFA (1.8 mL, 23.8 mmol) and the solution was stirred at room temperature for 1½ h. The reaction was concentrated in vacuo, azeotroping with toluene (×2) and dried in vacuum desiccator (containing KOH) overnight to give a yellow oil. The crude oil was dissolved in $^i$PrOH (4.4 mL) and both 2-amino-3-nitro-4,5-dichloropyridine (190 mg, 0.752 mmol) and DIPEA (520 µl, 3.00 mmol) were added. The solution was stirred at 50° C. for 4 h. On cooling, a yellow precipitate dropped out which was filtered, washed with Et$_2$O, dried in vacuo to yield the title compound as a yellow solid (165 mg, 0.486, 65%). The filtrate was concentrated in vacuo to give 715 mg oily yellow solid. Purification was accomplished by flash chromatography on silica gel (4×11) eluting with EtOAc/hexane (40-50%) to yield the title compound (42 mg, 16%) as a yellow solid.

$^1$H-NMR (500 MHz, CDCl$_3$) 2.74 (app t, J=4.1 Hz, 4H, —CH$_2$—), 3.25 (t, J=4.8 Hz, 4H, —CH$_2$—), 3.85 (s, 2H, —CH$_2$C—), 5.77 (s, 2H, NH$_2$), 7.99 (s, 1H, CH$_{ar}$), 8.72 (S, 1H, —C(Cl)CH—).

LC-MS (ESI, m/z): Rt=1.56 min-340, 342 [(M+H)$^+$, Cl isotopic pattern].

3-((4-(6-Chloro-2-(1,3-dimethyl-1H-pyrazol-4-yl)-3H-imidazo[4,5-b]pyridin-7-yl)piperazin-1-yl)methyl)-1,2,4-oxadiazole To a solution of 4-(4-((1,2,4-oxadiazol-3-yl)methyl)piperazin-1-yl)-5-chloro-3-nitropyridin-2-amine (50.0 mg, 0.147 mmol) and 1,3-dimethyl-1H-pyrazole-4-carbaldehyde (19.2 mg, 0.155 mmol) in EtOH (3.4 mL) was added 1M Na$_2$S$_2$O$_4$ (0.588 mL, 0.588 mmol, freshly prepared) and the solution was heated to 80° C. and stirred for 15 h whilst being open to air. Once cooled, the reaction was evaporated in vacuo and the residue dry loaded onto silica. Purification was accomplished by flash chromatography on silica gel (2×14) eluting with MeOH/CH$_2$Cl$_2$ (5-7.5%) to yield the title compound (26 mg, 43%) as a pale yellow solid.

$^1$H-NMR (500 MHz, CDCl$_3$) 2.58 (s, 3H, CH$_3$), 2.81 (app t, J=4.4 Hz, 4H, CH$_2$), 3.82 (app s, 4H, CH$_2$), 3.85 (s, 3H, NCH$_3$), 3.88 (S, 2H, —CH$_2$—), 7.62 (br s, 1H, CH$_{ar}$), 7.87 (br s, 1H, CH$_{ar}$), 8.74 (s, 1H, CH$_{ar}$), 13.04 (s, 1H, NH);

LC-MS (ESI, m/z): Rt=1.91 min-414, 416 [(M+H)$^+$, Cl isotopic pattern];

HRMS: Found: 436.1374, calculated for C$_{18}$H$_{20}$N$_9$OClNa (M+Na)$^+$: 436.1372.

Example 3

Preparation of 3-((4-(6-Chloro-2-(1,3-dimethyl-1H-pyrazol-4-yl)-3H-imidazo[4,5-b]pyridin-7-yl)piperazin-1-yl)methyl)-5-methyl-1,2,4-oxadiazole

2-Amino-5-chloro-4-(4-(5-methyl-1,2,4-oxadiazol-3-yl)methylpiperazin-1-yl)-3-nitropyridine 1-[(5-Methyl-1,2,4-oxadiazol-3-yl)methyl]piperazine hydrochloride (217 mg, 0.99 mmol) and 2-amino-4,5-dichloro-3-nitropyridine (208 mg, 1.0 mmol) were stirred in 2-propanol (5 mL) and diisopropylethylamine (523 µL, 387 mg, 3.0 mmol) was added. The mixture was stirred and heated at 45° C. for 23 h. The reaction was cooled and the product filtered off and washed with 2-propanol. Drying in vacuum gave the product (246 mg, 69%). $^1$H-NMR (500 MHz, CDCl$_3$), 2.63 (s, 3H, CH$_3$), 2.77 (br m, 4H, piperazine C—H), 3.29 (m, 4H, piperazine C—H), 3.76 (s, 2H, CH$_2$), 5.27 (s, 2H, NH$_2$), 8.02 (s, 1H, pyridine 6-H).

LC-MS (ESI, m/z): Rt=1.66 min-354 (M+H)$^+$, $^{35}$Cl isotope.

3-((4-(6-Chloro-2-(1,3-dimethyl-1H-pyrazol-4-yl)-3H-imidazo[4,5-b]pyridin-7-yl)piperazin-1-yl)methyl)-5-methyl-1,2,4-oxadiazole To a solution of 5-chloro-4-(4-((5-methyl-1,2,4-oxadiazol-3-yl)methyl)piperazin-1-yl)-3-nitropyridin-2-amine (60.0 mg, 0.170 mmol) and 1,3-dimethyl-1H-pyrazole-4-carbaldehyde (22.2 mg, 0.179 mmol) in EtOH (3.8 mL) was added 1M $Na_2S_2O_4$ (0.678 mL, 0.678 mmol, freshly prepared) and the solution was heated to 80° C. and stirred for 16 h whilst being open to air. Once cooled, the reaction was evaporated in vacuo and the residue dry loaded onto silica. Purification was accomplished by flash chromatography on silica gel (3×14) eluting with $MeOH/CH_2Cl_2$ (5-7.5%) to yield the title compound as a pale yellow solid. Recrystallisation in EtOAc/$Et_2O$ gave the title compound (20 mg, 27%) as an off white solid. The filtrate was concentrated in vacuo, an additional amount of title compound (12 mg, 16%) as a pale yellow solid. $^1$H-NMR (500 MHz, $CDCl_3$) 2.60 (s, 3H, $CH_3$), 2.62 (s, 3H, $CH_3$), 2.81 (app t, J=4.5 Hz, 4H, $CH_2$), 3.76 (s, 2H, —$CH_2$—), 3.87 (app s, 4H, $CH_2$), 3.90 (s, 3H, $NCH_3$), 7.77 (br s, 1H, $CH_{ar}$), 7.96 (br S, 1H, $CH_{ar}$), 12.18 (s, 1H, NH);

LC-MS (ESI, m/z): Rt=1.95 min-428, 430 [(M+H)$^+$, Cl isotopic pattern];

HRMS: Found: 450.1527, calculated for $C_{19}H_{22}N_9OClNa$ (M+Na)$^+$: 450.1528.

Evaluation of the Compounds of Examples 1 to 3
General Materials and Methods

Aurora kinase assays: Aurora kinase $IC_{50}$ values were determined as previously described.[26, 36]

Cell viability assay: $GI_{50}$ values (50% cell growth inhibitory concentration) were determined as previously described.[26, 36]

Determination of Cellular $IC_{50}$ Values of Example 1 for Aurora A and Aurora B Inhibition:

Myc-tagged Aurora A was transfected in Hela cells using Lipofectamine LTX in 24 well plates, and 24 hours after transfection, cells were treated with different concentrations of Example 1 for 2 hours. Cells were then lysed in 2×LDS sample buffer. Proteins from different samples were resolved by 4-12% Bis-Tris NuPage (Invitrogen) gels and analysed by western blotting using P-histone H3 (S10) and P-Aurora A (T288) antibodies. The bands for P-histone H3 and P-Aurora A were quantified using Image J software and $IC_{50}$ values were calculated using Graphpad Prism.

Mouse Liver Microsomal Stability:

Compounds (10 μM) were incubated with male CD1 mouse liver microsomes (1 mg·mL$^{-1}$) protein in the presence of NADPH (1 mM), UDPGA (2.5 mM) and $MgCl_2$ (3 mM) in phosphate buffered saline (10 mM) at 37° C. Incubations were conducted for 0 and 30 minutes. Control incubations were generated by the omission of NADPH and UDPGA from the incubation reaction. The percentage compound remaining was determined after analysis by LCMS.

Human Liver Microsomal Stability:

Compounds (10 μM) were incubated with mixed gender pooled human liver microsomes (1 mg·mL$^{-1}$) protein in the presence of NADPH (1 mM), UDPGA (2.5 mM) and $MgCl_2$ (3 mM) in phosphate buffered saline (10 mM) at 37° C. Incubations were conducted for 0 and 30 minutes. Control incubations were generated by the omission of NADPH and UDPGA from the incubation reaction. The percentage compound remaining was determined after analysis by LCMS.

hERG inhibition: All hERG percentage inhibitions at 10 μM compound concentration were determined by Millipore in a high-throughput cell-based electrophysiology assay for inhibition of hERG tail current[41], and values are reported as a mean of multiple determinations. 0.3% DMSO aqueous vehicle negative control gave 7-16% inhibition. Cisapride (1 μM) positive control gave 96-104% inhibition. All hERG $IC_{50}$ values were determined by Millipore,[41] and the hERG $IC_{50}$ for Example 1 was also determined by Cyprotex plc measuring hERG tail-currents by whole-cell voltage-clamping.[42]

Physicochemical properties: Log D and pKa measurements were performed by Pharmorphix® Solid State Services, Member of the Sigma-Aldrich Group, Cambridge, UK.

Kinase selectivity profiling: Kinase profiling using the KINOMEScan™ technology and Kd determinations were performed by KINOMEscan, a Division of DiscoveRx Corporation, San Diego, Calif., USA; www.kinomescan.com.

In vivo full PK (compound of Example 1): Mice (female Balb/C) were dosed p.o. or i.v. with the compound of Example 1 (5 mg kg$^{-1}$) in 10% DMSO, 5% Tween 20 in saline. After administration, mice were sacrificed at 5, 15, and 30 minutes and 1, 2, 4, 6 and 24 h. Blood was removed by cardiac puncture and centrifuged to obtain plasma samples. Plasma samples (100 μL) were added to the analytical internal standard (Olomoucine; IS), followed by protein precipitation with 300 μL methanol. Following centrifugation (1,200×g, 30 min, 4° C.), the resulting supernatants were analysed for the compound of Example 1 levels by LCMS using a reverse-phase Acquity UPLC C18 (Waters, 50×2.1 mm) analytical column and positive ion mode ESI MRM on an Agilent 1200 liquid chromatography system coupled to a 6410 triple quadrupole mass spectrometer (Agilent Ltd.).

Human tumour xenograft efficacy study: Procedures involving animals were carried out within guidelines set out by The Institute of Cancer Research's Animal Ethics Committee and in compliance with national guidelines: Workman P, Aboagye E O, Balkwill F, Balmain A, Bruder G, Chaplin D J, Double J A, Everitt J, Farningham D, Glennie M J, Kelland L R, Robinson V, Stratford I J, Tozer G M, Watson S, Wedge S R, Eccles S A. Guidelines for the welfare and use of animals in cancer research. *Brit J Cancer* 102: 1555-1577, 2010.

Female CrTacNCr-Fox1(nu) athymic mice were implanted subcutaneously with 10$^7$ FLT3-ITD MV4-11 leukaemia cells. When the xenografts were well established (10 days after implantation, mean tumour volumes of at least 100 mm$^3$) animals were treated with either vehicle (10% DMSO, 20% PEG 400, 5% Tween 80 and 65% water) or the compound of Example 1 administered orally at two doses, 50 mg/kg and 100 mg/kg (n=5 per group). Dosing was twice daily for 7 days, and once daily for a further 4 days.

PK/PD study: A 4-day PK/PD study was performed by oral administration of vehicle as above or 50 mg/kg and 100 mg/kg of the compound of Example 1 twice daily in athymic mice bearing well-established MV4-11 xenografts (17 days after implantation). Plasma and tumour samples were collected 2 h and 6 h after the final doses.

Results

Aurora Kinase Activity, Cell Activity, Microsomal Stability, hERG Inhibition and Physicochemical Properties The activity of the exemplified compounds against Aurora A (biochemical assay), cell-based GI50 in SW620 cells and hERG is shown in the Table 1 below together with data relating to the microsomal stability of these compounds and their respective clogP values.

TABLE 1

| Example No. | Aurora-A IC$_{50}$ (μM) | SW620 GI$_{50}$ (μM) | MLM/HLM[b] | hERG IC$_{50}$ (μM) | clogP[27] |
|---|---|---|---|---|---|
| Ex. 56 of WO2007/072017 | 0.032[a] | n.d. | | 5.5 | 2.78 |
| Ex. 57 of WO2007/072017 | 0.300[a] | n.d. | | 10.8 | 2.72 |
| 1 | 0.038 ± 0.029 | 0.283 ± 0.227 | 34%/10% | >25 | 4.81[c] |
| 2 | 0.040 ± 0.015 | 1.175 ± 0.653 | 67%/22% | 11.0 | 1.45 |
| 3 | 0.052[a] | 1.1[a] | 58%/20% | 9.5 | 1.72 |

For Aurora-A IC$_{50}$ and SW620 GI$_{50}$ determinations, results are mean values of two independent determinations or mean (±SD) for n > 2 unless specified otherwise.
[a]Results are mean values for samples run in triplicate.
[b]MLM/HLM: Percentage of parent compound metabolised after a 30 min incubation.
[c]LogD7.4 = 3.84 (experimentally determined value).
n.d. = not determined.

The compound of Example 1 showed a lower inhibitory activity against hERG when compared to the compounds of Examples 56 and 57 of WO2007/072017.

Based on these results, the compound of Example 1 was selected for further in vitro and in vivo characterisation.

Kinase Selectivity

The kinase selectivity was assessed by profiling Example 1 in a 442-kinase panel (386 non-mutant kinases) at a concentration of 1 μM using the KINOMEScan™ technology.[28] The S(10) selectivity score that is calculated by dividing the number of non-mutant kinases for which >90% competition was observed in the assay (this is measured as <10% of control) by the total number of non-mutant kinases tested, was determined as 0.057, i.e. 22 hits from the 386 non-mutant kinases tested. Aurora-A, -B, and -C were potently inhibited with % control values determined as 3.4%, 1%, and 16% respectively. This primary screening also revealed greater than 94% competition for FLT3 kinase and FLT3 mutants including FLT3-ITD, FLT3(D835Y), and FLT3(D835H).

The FLT3 and Aurora inhibitory activities of the compound of Example 1 were subsequently confirmed by Kd value determination (KINOMEScan™ technology), as shown in Table 2.

TABLE 2

Kd values for the compound of Example 1

| Kinase | Kd (nM) |
|---|---|
| Aurora-A | 7.5 |
| Aurora-B | 48 |
| FLT3 | 6.2 |
| FLT3(D835H) | 11 |
| FLT3(D835Y) | 14 |
| FLT3-ITD | 38 |
| FLT3(K663Q) | 5.1 |
| FLT3(N841I) | 16 |
| FLT3(R834Q) | 110 |

Examples 2 and 3 were also potent inhibitors of FLT3 and FLT3-ITD. The Kd values of Example 2 against FLT3 and FLT3-ITD were determined as 4.4 nM and 14 nM respectively. Likewise, the Kd values of Example 3 against FLT3 and FLT3-ITD were determined as 5.6 nM and 26 nM respectively.

Taken together, this data indicate that the compound of Example 1 is a potent dual inhibitor of FLT3 and Aurora kinases with few off target kinase activities across the kinome.

Cellular Assay Evaluation

Consistent with a dual FLT3/Aurora inhibitory activity, the compound of Example 1 displayed antiproliferative activity in a range of human tumour cell lines, including HCT116 human colon carcinoma (GI$_{50}$=0.300 μM), and the human FLT3-ITD positive AML cell lines MOLM-13 (GI$_{50}$=0.104 μM) and MV4-11 (GI$_{50}$=0.291 μM). In Hela cells, the compound of Example 1 inhibited both cellular Aurora-A and Aurora-B with IC$_{50}$ values of 0.030 μM and 0.148 μM respectively. In these cell-based assays, the reduction of H3 phosphorylation at S10 was used as a biomarker for Aurora-B inhibition, and the autophosphorylation of Aurora-A on T288 as a biomarker for Aurora-A inhibition.[29]

In Vivo PK

The in vivo PK results for the compound of Example 1 in mouse are shown in Table 3. It is a highly orally bioavailable compound (F=100%) with clearance determined as 0.058 L/h (~48 mL/min/kg) and Vd as 0.066 L (~3.3 L/kg).

TABLE 3

Compound of Example 1: Mouse plasma protein binding, and PK parameters (iv dosing: 5 mg/kg, oral dosing: 5 mg/kg)

| PPB (mouse) | t½, (iv) (h) | Cl, (iv) (L/h) | AUCinf, (iv) h · nmol/L | Vd (L) | F % (po) |
|---|---|---|---|---|---|
| 97.3 ± 0.8 | 0.84 | 0.058 | 3753 | 0.066 | 100 |

AML Xenograft Model

Figure 1:
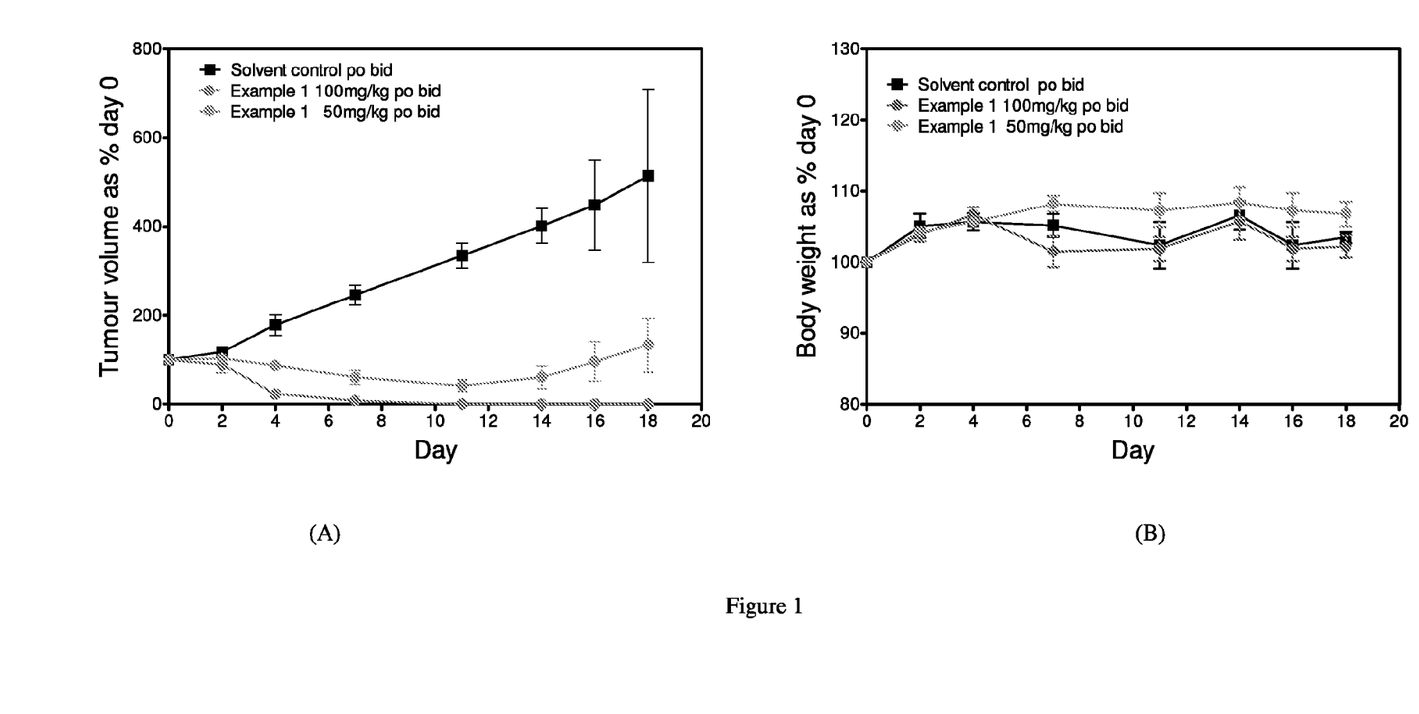
FIG. 1 shows the efficacy of the compound of Example 1 against MV4-11 human tumour xenografts in athymic mice: (A) Relative tumour volumes±SEM. (B) Mouse body weights.

Activity of the compound of Example 1 in a human AML xenograft model is shown in FIG. 1.

Referring to FIG. 1, it can be seen that the compound of Example 1 strongly inhibited the growth of MV4-11 human tumour xenografts in a dose dependent manner with no observed toxicity as defined by body weight loss. When therapy was discontinued after 11 days, tumours were undetectable in mice treated with 100 mg/kg dosing schedule of the compound of Example 1 and had decreased to 42% of the initial volume in mice treated with 50 mg/kg dosing schedule. Control mice were culled on day 18 from the start of therapy when the mean tumour volume had increased by over 500%. In contrast, single mice were culled when tumours progressed to this stage as follows: days 28 and 31 at 50 mg/kg and days 46 and 56 at 100 mg/kg. Three out of 5 mice in each treatment group (60%) failed to develop progressively growing tumours at the time the study was terminated on day 60.

Figure 2:
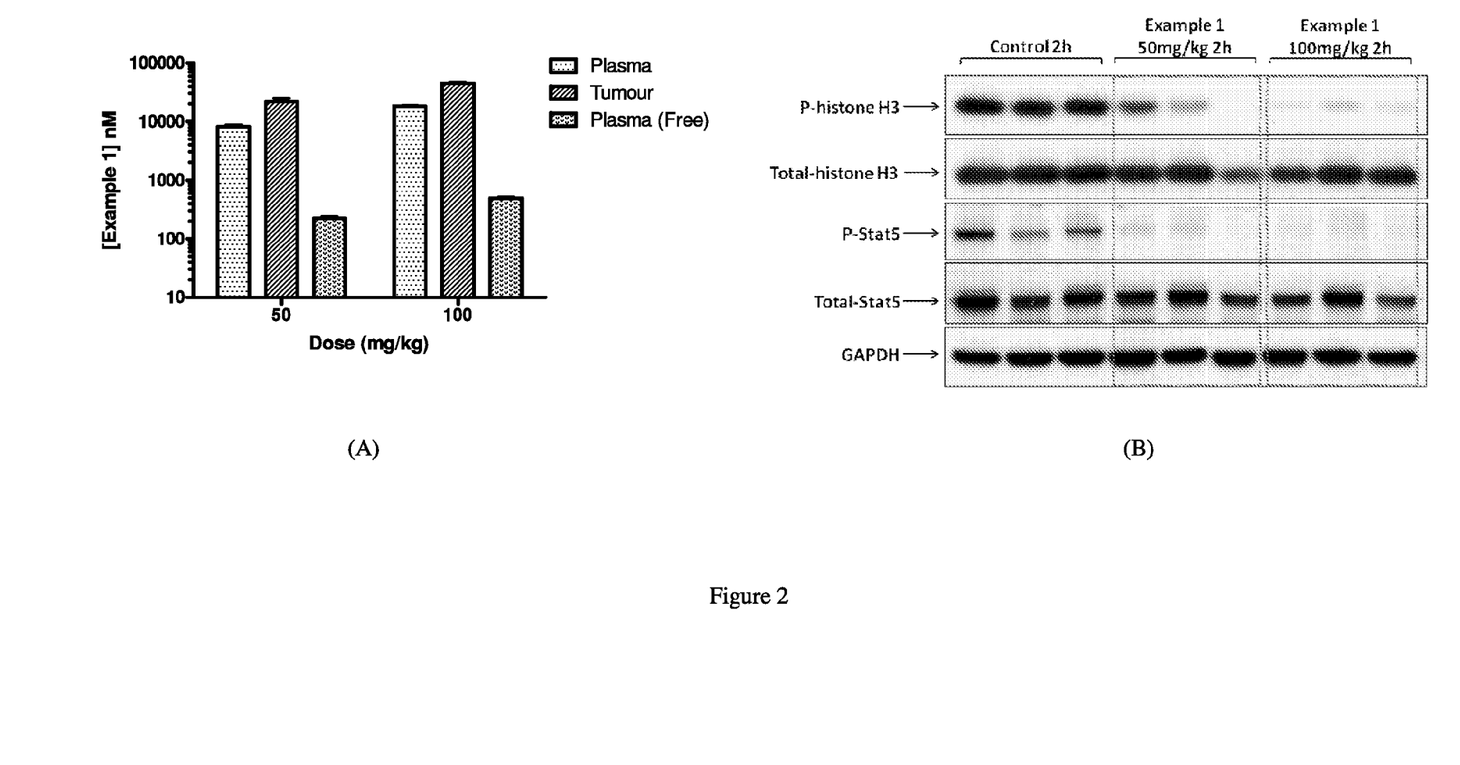
FIG. 2 shows: (A) Total plasma and tumour drug concentrations and free plasma drug concentrations following dosing at 50 and 100 mg/kg, samples taken 2 h post final dose. (B) Compound of Example 1 inhibits histone H-3 phosphorylation at S10, and the phosphorylation of STAT5 at Y694 in MV4-11 human tumour xenografts (4-day study).

As a result of this potent in vivo inhibitory effect, tumours on treatment were too small to provide material for a pharmacokinetic/pharmacodynamic analysis. Subsequently, a repeat 4-day PK/PD study was performed by oral administration of 50 mg/kg and 100 mg/kg of Example 1 twice daily. Pharmacodynamic analysis showed a clear inhibition of histone H-3 phosphorylation, and inhibition of STAT5 phosphorylation which is a downstream target of FLT3 (FIG. 2). In addition, plasma free drug concentration in samples obtained 2 h after the final dose, were determined as 222 nM and 488 nM for the 50 mg/kg and 100 mg/kg dosing schedules respectively (FIG. 2). The plasma free drug concentrations are clearly above the Kd values of the compound of Example 1 against the relevant kinases, i.e. Aurora-A (Kd=7.5 nM), Aurora-B (Kd=48 nM), FLT3 (Kd=6.2 nM), FLT3-ITD (Kd=38 nM). These finding demonstrate that the compound of Example 1 significantly inhibits the growth of a FLT3-ITD positive AML human xenograft model in vivo, with biomarker modulation and free drug exposure consistent with dual FLT3 and Aurora kinase target engagement.

Inhibition of Cytochrome P450 Isoforms

Materials and Methods

Two comparator compounds were used in this study, namely 6-bromo-2-(1-methyl-1H-pyrazol-4-yl)-7-(4-(pyridine-3-ylmethyl)piperazin-1-yl)-3H-imidazo[4,5-b]pyridine (Comparator 1, Example 56, WO2007/072017) and 6-bromo-7-(4-(pyridine-3-ylmethyl)piperazin-1-yl)-2-(1,3,5-trimethyl-1H-pyrazol-4-yl)-3H-imidazo[4,5-b]pyridine (Comparator 2, Example 57, WO2007/072017).

The comparator compounds and the compounds of Examples 1 to 3 above were incubated with human liver microsomes (0.5 mg·ml$^{-1}$) at 1 µM, 10 µM and 50 µM.

Inhibition of CYP isozymes was determined using a mixture of probe substrates (Table 4). The samples were incubated for 10 minutes followed by protein precipitation with methanol. The substrate metabolites in each sample were measured by LC/MS/MS using reverse-phase liquid chromatography and positive ion mode ESI with multiple reaction monitoring (MRM).

TABLE 4

CYP isozymes probe substrate concentrations and metabolites detected

| Enzyme | Probe Substrate | Substrate concentration (µM) | Literature Km (µM) | Metabolite |
|---|---|---|---|---|
| CYP1A2 | Phenacetin | 10 | 10-50 | Acetominophen |
| CYP2A6 | Coumarin | 5 | 0.5-2 | 7-Hydroxycoumarin |
| CYP2C9 | Tolbutamide | 60 | 100-200 | 4-Hydroxytolbutamide |
| CYP2C19 | Mephenytoin | 40 | 30-50 | (+/−)-Hydroxy-mephenytoin |
| CYP2D6 | Bufuralol | 5 | 4-10 | 1-Hydroxybufuralol |
| CYP3A4 | Midazolam | 3 | 3-5 | 1-Hydroxymidazolam |

Results

TABLE 5

Estimated IC$_{50}$ values for the inhibition of human CYP isozymes by the test compounds

| | CYP1A2 | CYP2A6 | CYP2C9 | CYP2C19 | CYP2D6 | CYP3A4 |
|---|---|---|---|---|---|---|
| Comparator 1 | 10-50 µM | >50 µM | 10-50 µM | 10-50 µM | 1-10 µM | <1 µM |
| Comparator 2 | >50 µM | >50 µM | 10-50 µM | 10-50 µM | 10-50 µM | <1 µM |
| Example 1 | >50 µM | >50 µM | 10-50 µM | 10-50 µM | 10-50 µM | >50 µM |
| Example 2 | >50 µM | >50 µM | 10-50 µM | 10-50 µM | 10-50 µM | >50 µM |
| Example 3 | >50 µM | >50 µM | 10-50 µM | >50 µM | 10-50 µM | >50 µM |

Examples 1-3 did not show any significant inhibition of CYP isozymes (Table 5), the estimated IC$_{50}$ values were higher than 10 µM.

No compounds showed significant inhibition of CYP1A2, CYP2A6, CYP2C9 or CYP2C19. Both comparator compounds showed significant inhibition of CYP3A4 with approximated IC$_{50}$s being below 1 µM, with Comparator 1 also inhibiting CYP2D6. The compounds of the present invention therefore possessed significantly reduced CYP3A4 inhibition relative to both of the comparator compounds.

REFERENCES

1. Carmena, M et al.; *Nat. Rev. Mol. Cell Biol.* 2003, 4, 842-854.
2. Ducat D. et al.; *Exp. Cell Res.* 2004, 301, 60-67.
3. Marumoto, T. et al.; *Nat. Rev. Cancer* 2005, 5, 42-50.
4. Barr, A. R. et al. *J. Cell Sci.* 2007, 120, 2987-2996.
5. Bayliss, R et al.; *Mol. Cell.* 2003, 12, 851-862.
6. Giet, R. et al.; *J. Cell Biol.* 2001, 152, 669-681.
7. Gassmann, R. et al.; *J. Cell Biol.* 2004, 166, 179-191.
8. Sessa, F. et al.; *Mol. Cell,* 2005, 18, 379-391.
9. Bishop, J. D. et al.; *J. Biol. Chem.* 2002, 277, 27577-27580.
10. Tanaka, T. et al.; *Cancer Res.* 1999, 59, 2041-2044.
11. Bischoff, J. R. et al.; *EMBO J.* 1998, 17, 3052-3065.
12. Gritsko, T. M. et al.; *Clin. Cancer. Res.* 2003, 9, 1420-1426.
13. Reichardt, W. et al.; *Oncol. Rep.* 2003, 10, 1275-1279.
14. Chieffi, P. et al.; *J. Endocrinol.* 2004, 181, 263-270.
15. Araki, K. et al.; *J Neurooncol.* 2004, 67, 53-64.
16. Sorrentino, R. et al.; *J Clin Endocrinol Metab.* 2005, 90, 928-935.
17. Kimura, M. et al.; *J. Biol. Chem.* 1999, 274, 7334-7340.
18. Pollard, J. R. et al.; *J. Med. Chem.* 2009, 52, 2629-2651.
19. Green, M. R. et al.; *Expert Opin. Drug Discov.* 2011, 6, 291-307.
20. Cheung, C. H. A. et al.; *Expert Opin. Ther. Patents* 2011, 21, 857-884.
21. Harrington, E. A. et al.; *Nat. Med.* 2004, 10, 262-267.
22. Mortlock, A. A. et al.; *J. Med. Chem.* 2007, 50. 2213-2224.
23. Fancelli, D. et al.; *J. Med. Chem.* 2006, 49, 7247-7251.
24. Caprinelli. P. et al.; *Mol. Cancer Ther.* 2007, 6, 3158-3168.
25. Payton, M. et al.; *Cancer Res* 2010, 70, 9846-9854.
26. Bavetsias, V. et al.; *J. Med Chem.* 2010, 53, 5213-5228.
27. CLogP was calculated using ChemBioDraw Ultra 12 by CambridgeSoft (www.cambridgesoft.com).
28. Kinase profiling using the KINOMEScan™ technology: www.kinomescan.com.
29. Manfredi, M. G. et al.; *Proc. Natl. Acad. Sci. USA* 2007, 104, 4106-4111.
30. Ikezoe, T. et al.; *Mol Cancer Ther* 2007, 6, 1851-1857.
31. Ochi, T. et al.; *Blood* 2009, 113, 66-74.
32. Huang, X.-F. et al.; *Blood* 2008, 111, 2854-2865.
33. Walsby, E. et al.; *Haematologica* 2008, 93, 662-669.
34. Meshinchi, S. et al; *Clin Cancer Res* 2009, 15, 4263-4269.
35. Meshinchi, S. et al.; *Blood* 2006, 108, 3654-3661.
36. Chan, F. et al.; *Mol Cancer Ther,* 2007, 6, 3147-3157.

37. Stirewalt, D. L. et al.; *Nat Rev Cancer* 2003, 3, 650-665.
38. Kindler, T. et al.; *Blood* 2010, 116, 5089-5102.
39. Levis, M. J.; Best Practice & Research Clinical Haematology 2010, 23, 489-494.
40. Bavetsias, V. et al, Bioorg. Med. Chem. Lett. 2007, 17, 6567-6571.
41. *Ion Channel Cardiac Profiler*; Millipore: Billerica, Mass.: http://www.millipore.com/life_sciences/flx4/ld_ion
42. hERG Safety Assay; Cyprotex plc, Cheshire, UK; www.cyprotex.com
43. Roden, D. M. *N. Engl. J. Med.* 2004, 350, 1013-1022.

What is claimed is:

1. A compound of formula I shown below:

I wherein:
  $R_1$ is Br or Cl;
  $R_2$ is selected from formula II or formula III shown below:

II

III wherein $R_a$ is hydrogen or methyl;
or a pharmaceutically acceptable salt or solvate thereof.

2. A compound according to claim 1, wherein $R_1$ is Cl.
3. A compound according to claim 1, wherein $R_1$ is Br.
4. A compound according to claim 1, wherein $R_2$ is of formula II.
5. A compound according to claim 1, wherein $R_2$ is of formula III.
6. A compound according to claim 1, which is selected from any one of:
  6-Chloro-7-(4-(4-chlorobenzyl)piperazin-1-yl)-2-(1,3-dimethyl-1H-pyrazol-4-yl)-3H-imidazo[4,5-b]pyridine;
  3-((4-(6-Chloro-2-(1,3-dimethyl-1H-pyrazol-4-yl)-3H-imidazo[4,5-b]pyridin-7-yl)piperazin-1-yl)methyl)-1,2,4-oxadiazole;
  3-((4-(6-Chloro-2-(1,3-dimethyl-1H-pyrazol-4-yl)-3H-imidazo[4,5-b]pyridin-7-yl)piperazin-1-yl)methyl)-5-methyl-1,2,4-oxadiazole;
or a pharmaceutically acceptable salt or solvate thereof.

7. A pharmaceutical composition comprising a compound according to claim 1, or a pharmaceutically acceptable salt or solvate thereof, and one or more pharmaceutically acceptable excipients.

8. A method of treating a cancer, said method comprising administering to a subject in need of such treatment a therapeutically effective amount of a compound of formula I shown below:

I wherein:
  $R_1$ is Br or Cl;
  $R_2$ is selected from formula II or formula III shown below:

II

III wherein $R_a$ is hydrogen or methyl;
or a pharmaceutically acceptable salt or solvate thereof,
wherein the cancer is a leukemia, and
wherein the leukemia is acute myeloid leukemia (AML).

9. The method of claim 8, wherein the compound is selected from the group consisting of 6-Chloro-7-(4-(4-chlorobenzyl)piperazin-1-yl)-2-(1,3-dimethyl-1H-pyrazol-4-yl)-3H-imidazo [4,5-b]pyridine; 3-((4-(6-Chloro-2-(1,3-dimethyl-1H-pyrazol-4-yl)-3H-imidazo [4,5-b]pyridin-7-yl)piperazin-1-yl)methyl)-1,2,4-oxadiazole; 3-((4-(6-Chloro-2-(1,3-dimethyl-1H-pyrazol-4-yl)-3H-imidazo [4,5-b] pyridin-7-yl)piperazin-1-yl)methyl)-5-methyl-1,2,4-oxadiazole; or a pharmaceutically acceptable salt or solvate thereof.

* * * * *